(12) United States Patent
Kaji

(10) Patent No.: US 8,901,493 B2
(45) Date of Patent: Dec. 2, 2014

(54) ELECTRON MICROSCOPE

(75) Inventor: Kazutoshi Kaji, Hitachi (JP)

(73) Assignee: Hitachi High-Technologies Corporation, Tokyo (JP)

(*) Notice: Subject to any disclaimer, the term of this patent is extended or adjusted under 35 U.S.C. 154(b) by 0 days.

(21) Appl. No.: 13/514,306

(22) PCT Filed: Oct. 25, 2010

(86) PCT No.: PCT/JP2010/006291
§ 371 (c)(1),
(2), (4) Date: Jun. 7, 2012

(87) PCT Pub. No.: WO2011/070704
PCT Pub. Date: Jun. 16, 2011

(65) Prior Publication Data
US 2012/0241611 A1    Sep. 27, 2012

(30) Foreign Application Priority Data

Dec. 8, 2009 (JP) ................................ 2009-278105

(51) Int. Cl.
*G01N 23/04* (2006.01)
*H01J 37/26* (2006.01)
*H01J 37/244* (2006.01)
*G01N 23/222* (2006.01)
*H01J 37/06* (2006.01)

(52) U.S. Cl.
CPC ........... *H01J 37/244* (2013.01); *H01J 2237/28* (2013.01); *G01N 23/04* (2013.01); *H01J 2237/24415* (2013.01); *H01J 37/26* (2013.01); *G01N 2223/102* (2013.01); *H01J 2237/24485* (2013.01); *H01J 2237/24495* (2013.01); *G01N 2223/3037* (2013.01)
USPC .......................................... 250/310; 250/311

(58) Field of Classification Search
USPC .......................................................... 250/310
See application file for complete search history.

(56) References Cited

U.S. PATENT DOCUMENTS 4,253,154 A * 2/1981 Russ et al. ..................... 250/311
4,922,442 A * 5/1990 Bolk et al. ................. 250/363.02
(Continued)

FOREIGN PATENT DOCUMENTS

JP    2000-113854 A    4/2000
JP    2001-21511 A    1/2001
(Continued)

OTHER PUBLICATIONS

International Search Report with English translation dated Jan. 11, 2011 (four (4) pages).

(Continued)

*Primary Examiner* — Phillip A Johnston
*Assistant Examiner* — Sean Luck
(74) *Attorney, Agent, or Firm* — Crowell & Moring LLP

(57) ABSTRACT

An object of the present invention relates to measurement of a quantitative element image with a high S/N ratio and measurement of an electron energy loss spectrum with high energy precision and energy resolution. The present invention relates to measurement of a characteristic X-ray spectrum obtained by correcting dead time due to excessive X rays and measurement of an electron energy loss spectrum obtained by correcting energy based on a zero loss peak in the case where the characteristic X-ray spectrum and the electron energy loss spectrum are measured by irradiating one irradiation position on a sample with an electron beam for a predetermined time while scanning the surface of the sample to observe a Z-contrast image. According to the present invention, it becomes possible to measure a quantitative element image with a high S/N ratio by a characteristic X ray, an element image with a high S/N ratio by an electron energy loss spectrum and a high energy resolution spectrum.

6 Claims, 4 Drawing Sheets

(56) References Cited

U.S. PATENT DOCUMENTS

| | | | |
|---|---|---|---|
| 7,342,997 B2 * | 3/2008 | Ueda et al. | 378/71 |
| 7,351,967 B2 * | 4/2008 | De Robillard | 250/307 |
| 7,372,029 B2 * | 5/2008 | Tsuneta et al. | 250/311 |
| 7,642,513 B2 * | 1/2010 | Pinna et al. | 250/305 |
| 2004/0183011 A1 | 9/2004 | Kaji et al. | |
| 2009/0194691 A1 * | 8/2009 | Kaji | 250/311 |
| 2009/0242766 A1 * | 10/2009 | Terada et al. | 250/311 |

FOREIGN PATENT DOCUMENTS

| | | |
|---|---|---|
| JP | 2002-157973 A | 5/2002 |
| JP | 2009-170241 A | 7/2009 |
| JP | 2009-244001 A | 10/2009 |

OTHER PUBLICATIONS

Form PCT/ISA/237 (three (3) pages).

David B. Williams et al., "Transmission Electron Microscopy IV", Spectrometry IV, Kluwer Academics/ Plenum Publishers, 1996 (Five (5) pages).

R. F. Egerton, "Electron Energy-Loss Spectroscopy in the Electron Microscope" Second Edition, Kluwer Academics/ Plenum Publishers, Springer, 1996, Chapter 5, (Four (4) pages).

* cited by examiner

101

201

301

ELECTRON MICROSCOPE

TECHNICAL FIELD

The present invention relates to an electron microscope capable of measuring a characteristic X-ray spectrum and an electron energy loss spectrum.

BACKGROUND ART

As semiconductor elements and magnetic head elements have been minimized and downsized, these elements are now constituted from thin films of several nm (nanometers) stacked in an area of submicron size. In development of elements, it is important to analyze the structure and element distribution in such a minute area. Examples of a device for elementary analysis include a characteristic X-ray spectrometer and an electron energy loss spectrometer (also referred to as an energy filter).

In "Transmission Electron Microscopy (Non Patent Literature 1)," it is disclosed that the characteristic X-ray spectrometer and the electron energy loss spectrometer are mounted on a Transmission Electron Microscope (TEM) or a Scanning Transmission Electron Microscope (STEM) in order to observe and specify the minute area of analysis target substances.

It is extremely effective for detailed material analysis to simultaneously measure a characteristic X-ray spectrum and an electron energy loss spectrum at the same position on a sample. In the case of measuring an element image with a good S/N ratio or measuring a characteristic X-ray spectrum and an electron energy loss spectrum by using the characteristic X-ray spectrometer or the electron energy loss spectrometer, a method of increasing observation time and thereby enhancing signal strength is generally used.

CITATION LIST

Non Patent Literature

Non Patent Literature 1
"Transmission Electron Microscopy" by David B. Williams, C. Barry Carter
Non Patent Literature 2
"Electron Energy Loss Spectroscopy in the Electron Microscope" by Egerton

SUMMARY OF INVENTION

Technical Problem

For observation of an element image with use of a characteristic X ray or for measurement of a characteristic X-ray spectrum, a method generally referred to as spectrum imaging is used. This method is performed when a characteristic X-ray spectrometer is mounted on a STEM. An electron beam scans the surface of a sample and a characteristic X ray emitted from the sample is analyzed per pixel, while at the same time, a STEM image is observed. However, since the strength of a detected characteristic X ray is weak, it is necessary to scan the sample with an electron beam for dozens of minutes to several hours.

The electron energy loss spectrometer detects an inelastic scattering electron beam. However, since the inelastic scattering cross section is small, a detection signal thereby is weak. In the case of observing an element image and an electron energy loss spectrum with a good S/N ratio by using the electron energy loss spectrometer, signal strength can be enhanced by increasing observation time in the same way as in the characteristic X-ray spectrometer.

When a measurement time required for an element image and a spectrum with a high S/N ratio is compared, measurement of a characteristic X-ray spectrum requires longer time than measurement of an electron energy loss spectrum. In some cases, the measurement time of the former is several to several dozen times longer than the latter. In order to measure the characteristic X-ray spectrum and the electron energy loss spectrum simultaneously at the same position of a sample, optimization of measurement time is an issue to be accomplished.

When a large number of X rays are emitted, a counting loss of X rays occurs in the characteristic X-ray spectrometer. The counting loss time is referred to as dead time. Since the emission amount of X rays when an electron beam scans a sample is different depending on the materials which constitute the sample, the dead time becomes also different. For observing an element distribution image obtained by a characteristic X ray, measurement is generally performed so that effectual measurement time except the dead time becomes the same in each pixel. In such a measuring method, the time of actual irradiation with an electron beam becomes different for every pixel. In the case of an electron energy loss spectrum simultaneously measured with a characteristic X ray, the signal strength depends on electron beam irradiation time if electron beam irradiation time is different for each pixel. This causes a problem that a quantitative electron energy loss spectrum cannot be obtained.

In measurement of an electron energy loss spectrum, long measurement time causes spectrum shift. This may causes deterioration of energy precision and energy resolution of the spectrum.

Further, in the case of measuring an electron energy loss spectrum of high energy resolution, the energy range which can be measured in one measurement is narrow (e.g., about 50 eV). Consequently, it is impossible to measure a plurality of elements at the same sample position.

An object of the present invention relates to measurement of a quantitative element image with a high S/N ratio and measurement of an electron energy loss spectrum with high energy precision and energy resolution.

Solution to Problem

The present invention relates to measurement of a characteristic X-ray spectrum provided by correcting dead time due to excessive X rays and measurement of an electron energy loss spectrum provided by correcting energy based on a zero loss peak in the case where the characteristic X-ray spectrum and the electron energy loss spectrum are measured by irradiating one irradiation position on a sample with an electron beam for a predetermined time while scanning the surface of the sample to observe a Z-contrast image.

The present invention also relates to obtaining a plurality of times an electron energy loss spectrum including core loss of an observation target element and an electron energy loss spectrum including a zero loss peak while irradiating one position with an electron beam for a predetermined time, and integrating the electron energy loss spectra including the core loss based on the zero loss peak to obtain an electron energy loss spectrum with a high S/N ratio and with high energy resolution.

The present invention also relates to obtaining a plurality of electron energy loss spectra different in energy range while irradiating one position with an electron beam for a predetermined time, and connecting these spectra to obtain an electron energy loss spectrum with a large energy range.

Advantageous Effects of Invention

According to the present invention, it becomes possible to measure a quantitative element image with a high S/N ratio by a characteristic X ray, an element image with a high S/N ratio by an electron energy loss spectrum, and a high energy resolution spectrum.

DESCRIPTION OF EMBODIMENTS

Figure 1:
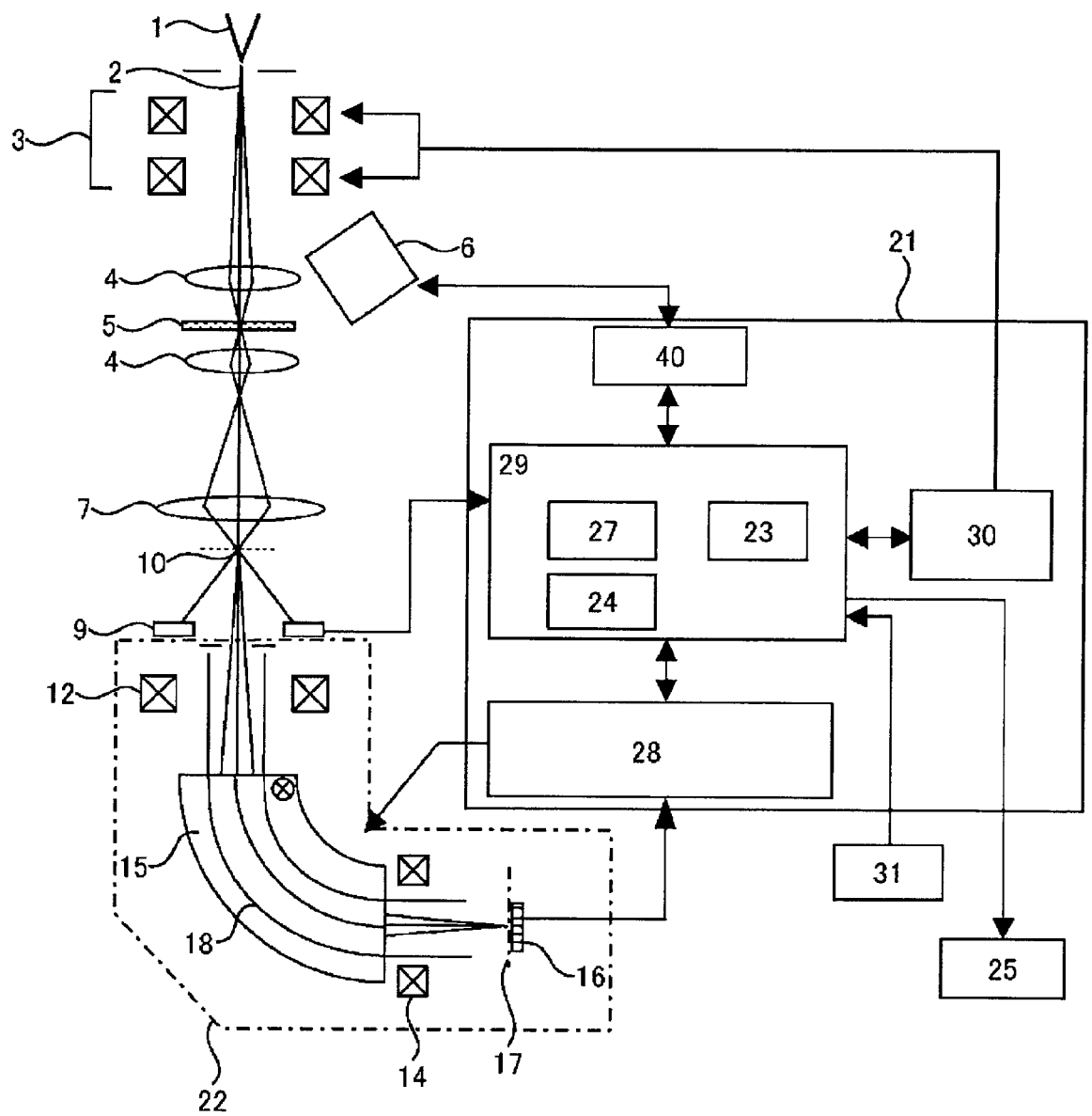
FIG. 1 is a view showing a schematic structure of an electron microscope in an embodiment 1.

An embodiment relates to an electron microscope having an elastic scattering electron detector, a characteristic X-ray spectrometer, and an electron energy loss spectrometer. More particularly, the present invention relates to an electron microscope capable of providing a quantitative element image and a characteristic X-ray spectrum with a high S/N ratio with use of a characteristic X-ray spectrometer as well as element image and electron energy loss spectrum with a high S/N ratio and high energy resolution with use of an electron energy loss spectrometer.

In an embodiment, an electron microscope is disclosed, including: an electron beam irradiation device for irradiating a sample with an electron beam emitted from an electron beam source; an electron energy loss spectrometer for analyzing energy of an electron beam made of inelastic scattering electrons which transmitted through the sample; a characteristic X-ray spectrometer for detecting a characteristic X ray emitted from the sample by irradiation of the electron beam and outputting a characteristic X-ray spectrum; and a control device for controlling the electron beam irradiation device, the electron energy loss spectrometer, and the characteristic X-ray spectrometer and obtaining an image relating to the sample, wherein the control device controls the electron beam irradiation device so that one irradiation position on the sample is irradiated with the electron beam for a predetermined time, obtains a characteristic X-ray spectrum detected by the characteristic X-ray spectrometer in the predetermined time, obtains a plurality of electron energy loss spectra detected by the electron energy loss spectrometer in the predetermined time, and controls so that a plurality of electron energy loss spectra outputted from the electron energy loss spectrometer have different energy ranges.

Also in an embodiment, an electron microscope is disclosed, including: an electron beam irradiation device for irradiating a sample with an electron beam emitted from an electron beam source; an electron energy loss spectrometer for analyzing energy of an electron beam made of inelastic scattering electrons which transmitted through the sample; a characteristic X-ray spectrometer for detecting a characteristic X ray emitted from the sample by irradiation of the electron beam and outputting a characteristic X-ray spectrum; and a control device for controlling the electron beam irradiation device, the electron energy loss spectrometer, and the characteristic X-ray spectrometer and performing line analysis relating to the sample, wherein the control device controls the electron beam irradiation device so that one irradiation position on the sample is irradiated with the electron beam for a predetermined time, obtains a characteristic X-ray spectrum detected by the characteristic X-ray spectrometer in the predetermined time, obtains a plurality of electron energy loss spectra detected by the electron energy loss spectrometer in the predetermined time, and controls so that a plurality of electron energy loss spectra outputted from the electron energy loss spectrometer have different energy ranges.

Also in an embodiment, an electron microscope is disclosed, in which a time when the characteristic X-ray spectrometer loses count of characteristic X rays is detected from the predetermined time, and the control device corrects strength of a characteristic X-ray spectrum which is obtained by correcting a counting loss time, and controls so that an electron energy loss spectrum in an energy range including a core loss peak of an element that is an analysis target and an electron energy loss spectrum in an energy range including a zero loss peak are included in a plurality of the electron energy loss spectra outputted from the electron energy loss spectrometer.

Also in an embodiment, an electron microscope is disclosed, including: an electron beam irradiation device for irradiating a sample with an electron beam emitted from an electron beam source; an electron energy loss spectrometer for analyzing energy of an electron beam made of inelastic scattering electrons which transmitted through the sample; a characteristic X-ray spectrometer for detecting a characteristic X ray emitted from the sample by irradiation of the electron beam and outputting a characteristic X-ray spectrum; and a control device for controlling the electron beam irradiation device, the electron energy loss spectrometer, and the characteristic X-ray spectrometer and obtaining an image relating to the sample or performing one-dimensional line analysis, wherein the electron energy loss spectrometer has a spectrum detector including a plurality of pixels for measuring an electron energy loss spectrum, the control device controls the electron beam irradiation device so that one irradiation position on the sample is irradiated with the electron beam for a predetermined time, and detects a time when the characteristic X-ray spectrometer loses count of characteristic X rays from the predetermined time, the control device corrects strength of a characteristic X-ray spectrum which is obtained by correcting a counting loss time, a plurality of spectra outputted from the electron energy loss spectrometer include an electron energy loss spectrum including a core loss peak of an element that is an analysis target and an electron energy loss spectrum including zero loss, the spectrum detector detects an amount of energy shift between an energy reference position predefined as a zero loss reference position and a pixel position at a zero loss peak, and energy of the electron energy loss spectrum is corrected based on the amount of energy shift.

Also in an embodiment, an electron microscope is disclosed, including: an electron beam irradiation device for irradiating a sample with an electron beam emitted from an electron beam source; an electron energy loss spectrometer for analyzing energy of an electron beam made of inelastic scattering electrons which transmitted through the sample; a characteristic X-ray spectrometer for detecting a characteristic X ray emitted from the sample by irradiation of the electron beam and outputting a characteristic X-ray spectrum; and a control device for controlling the electron beam irradiation device, the electron energy loss spectrometer, and the characteristic X-ray spectrometer and obtaining an image relating to the sample or performing one-dimensional line analysis, wherein the electron energy loss spectrometer has a spectrum detector including a plurality of pixels for measuring an electron energy loss spectrum, the control device controls the electron beam irradiation device so that one irradiation position on the sample is irradiated with the electron beam for a predetermined time, and detects a time when the characteristic X-ray spectrometer loses count of characteristic X rays from the predetermined time, the control device corrects strength of a characteristic X-ray spectrum which is obtained by correcting a counting loss time, a plurality of spectra outputted from the electron energy loss spectrometer in a predetermined time include an electron energy loss spectrum including a core loss peak of an element that is an analysis target and an electron energy loss spectrum including zero loss, and the electron energy loss spectrum is obtained a plurality of times in the predetermined time.

In an embodiment, an electron microscope is disclosed, including a control device for integrating a plurality of electron energy loss spectra.

In an embodiment, an electron microscope is disclosed, including a control device which detects by the spectrum detector an amount of energy shift between an energy reference position predefined as a zero loss reference position and a pixel position at a zero loss peak, and integrates a plurality of electron energy loss spectra after correcting energy of the electron energy loss spectra based on the amount of energy shift.

Hereinafter, the foregoing and other new characteristics and effects of the present invention will be described with reference to the drawings. In each of the drawings, like component members are designated by like reference numerals. It should be understood that embodiments are intended only illustrative of possible implementations of the invention and are not intended to limit the technical scope thereof. Moreover, respective embodiments may appropriately be combined and these combinations are disclosed in this specification.

Embodiment 1

(1) Structure of Scan Transmission Electron Microscope

FIG. 1 is a view showing the schematic structure of principal parts of a scan transmission electron microscope (STEM) having a characteristic X-ray spectrometer and an electron energy loss spectrometer (EELS). This scan transmission electron microscope is commonly used in each of the embodiments.

An electron beam 2 emitted from an electron beam emission source 1 forms a probe at an objective lens 4 and irradiates a sample 5. The position of the electron beam irradiating the sample 5 is deflected by an electron beam scanning coil 3. The sample irradiated with the electron beam emits a characteristic X ray, which is detected by a characteristic X-ray spectrometer 6. The electron beam which transmitted through the sample 5 forms an object point 10 of an electron energy loss spectrometer 22 with a projection lens 7. The electron beam then comes incident into the electron energy loss spectrometer 22. The electron energy loss spectrometer 22 analyzes energy of the electron beam, measures an electron energy loss spectrum and observes an element distribution image. The electron energy loss spectrometer 22 includes an energy dispersion section 15, a multipole lens 12 placed on the upstream side of the energy dispersion section 15, a quadruple lens 14 placed on the downstream side, an electron beam detector 16 for detecting an energy-dispersed electron beam, and a drift tube 18 for adjusting the energy of the electron beam. The number of multipole lenses 12 is not limited to one, and a plurality of multipole lenses may be combined.

A control device 21 includes a STEM control section 30, an electron energy loss spectrometer control section 28, a characteristic X-ray spectrometer control section 40, and a central controller 29. The STEM control section 30 is for controlling the electron beam position on a sample and guiding an electron beam to appropriately scan the sample. The electron energy loss spectrometer control section 28 controls electron beam energy analysis conditions of the electron energy loss spectrometer 22, such as, for example, excitation conditions of the energy dispersion section 15, focus conditions and amplification conditions of an electron energy loss spectrum, and applied voltage conditions of the drift tube 18. The characteristic X-ray spectrometer control section 40 controls an energy range of a specific X ray, a measurement time, and characteristic X-ray energy conditions of an observation target element and the like.

The central controller 29 has a database section 24, a memory section 27, and a calculation section 23. The database section 24 retains information on an element to be measured, control parameters for detecting a characteristic X ray of an observation target element, and control parameters of the electron energy loss spectrometer and the like. The memory section 27 stores detection signals from a Z-contrast detector 9 for observation of an elastic scattering electron image (also referred to as Z-contrast image) formed with elastic-scattering electrons, detection signals from the characteristic X-ray spectrometer 6, detection signals from the electron energy loss spectrometer 22 and the like. The calculation section 23 performs calculation for obtaining an element image and a characteristic X-ray spectrum from the characteristic X-ray signal detected by the characteristic X-ray spectrometer. The calculation section 23 also performs calculation for obtaining an element distribution image, an energy filter image, and an electron energy loss spectrum from the signals detected by the electron energy loss spectrometer 22.

The central controller 29 controls operation of the STEM control section 30, the characteristic X-ray spectrometer control section 40, and the electron energy loss spectrometer control section 28. The central controller 29 is also connected to an input device 31 for an operator to input (specify) an element to be measured and the like and to a display device 25 for displaying a characteristic X-ray spectrum, an electron energy loss spectrum, and an element distribution image.

(2) Measurement of Electron Energy Loss Spectrum and Observation of Element Distribution with Electron Energy Loss Spectrometer A description is now given of the operation inside the control device 21 at the time of measuring an electron energy loss spectrum and observing an element image with the electron energy loss spectrometer 22.

When an operator inputs (specifies) an element that he/she wants to observe with use of the input device 31, the central controller 29 retrieves pertinent element information from the database section 24 and outputs measurement conditions, which are peculiar to each element included in the element information, to the electron energy loss spectrometer control section 28. Based on the obtained measurement conditions, the electron energy loss spectrometer control section 28 controls the multipole lens 12, the quadruple lens 14, the drift tube 18, and the energy dispersion section 15, and makes an electron beam of an energy range including energy peculiar to the element come incident into the electron beam detector 16. In the case where the electron beam detector 16 has 1024 channels, an electron beam intensity signal becomes an electron energy loss spectrum. An electron beam detector having three channels may also be used. In that case, one channel may be used to detect an electron beam of the energy including core loss of the observed element and remaining two channels may be used to detect electron beams of low-loss energy which is lower than core loss energy. Thus, energy filter images of respective channels can be observed. In the case of generating an element image by using an energy filter image, the electron beam detector 16 needs at least two channels. More specifically, one channel is needed to obtain an energy filter image including core loss energy and at least one channel is needed to obtain a filter image of low-loss energy which is lower than the core loss energy for use in background image formation.

The electron beam intensity signal from the electron beam detector 16 is stored in the memory section 27. The calculation section 23 performs processings such as background correction of spectra, gain correction processing for the electron beam detector, integration processing of energy filter images and spectra, energy correction processing of spectra, processing for connecting spectra having different energy ranges, and calculation processing for obtaining an element image from energy filter images and spectra. The calculated spectra and element images are stored in the memory section 27 and are displayed on the display device 25. With such a series of processings, an operator can obtain a spectrum and an element distribution image. A Z-contrast image and an element distribution image which were simultaneously observed can also be displayed on the display device 25 (Z-contrast image and element image by an electron energy loss spectrum (B) 301 in FIG. 2).

It is to be noted that the electron beam detector 16 is not used only for measurement of electron energy loss spectra. For example, when an electron beam detector is structured to have two or more channels, electron beam detector simultaneously measures electron beams of different energy which were incident into respective channels, performs correction of the detector (e.g., sensitivity calibration and dark-current correction of the detector), and performs calculation with use of the electron beam intensity detected in each channel. As a result, an element distribution image can be observed. The calculation may be performed by using two-window method and three-window method described in "Electron Energy Loss Spectroscopy in the Electron Microscope (Non Patent Literature 2)." The electron beam detector 16 is not limited to a one-dimensional detector. A two-dimensional electron beam detector such as two-dimensional CCD may also be used. In that case, an electron energy loss spectrum can be measured by integrating vertical pixels in a direction of energy dispersion.

(3) Observation of Element Distribution with Characteristic X-Ray Spectrometer

A description is now given of the operation inside the control device 21 at the time of observing an element image with the characteristic X-ray spectrometer 6.

When an operator inputs (specifies) an element that he/she needs to observe with use of the input device 31, the central controller 29 retrieves pertinent element information from the database section 24 and outputs measurement conditions, which is peculiar to each element included in the element information, to the characteristic X-ray spectrometer control section 40. The characteristic X-ray spectrometer control section 40 controls a detection energy range and a measurement time of a characteristic X ray based on the obtained measurement conditions, and detects the characteristic X ray with the X-ray detector (not shown in FIG. 1) of the characteristic X-ray spectrometer 6.

The detected characteristic X ray is subjected to energy analysis and is stored in the memory section 27 as a characteristic X-ray spectrum or an element distribution image. At this point, the calculation section 23 performs calculation processing to correct dead time and obtain dead time-corrected characteristic X-ray spectrum and element distribution image. The spectrum and element image after calculation processing are stored in the memory section 27 and are also displayed on the display device 25 (element image by characteristic X rays (A) 201 in FIG. 2). Correction of dead time may be implemented by, for example, dividing a characteristic X ray spectrum by an effectual spectrum measurement time. With such a series of processings, an operator can obtain a spectrum and an element distribution image.

(4) Simultaneous Measurement of Spectra with Characteristic X-Ray Spectrometer and Electron Energy Loss Spectrometer A description is further given of measurement of quantitative element image and characteristic X-ray spectrum with a high S/N ratio, as well as element image and electron energy loss spectrum with a high S/N ratio and high energy resolution with use of the characteristic X-ray spectrometer 6 and the electron energy loss spectrometer 22.

Figure 2:
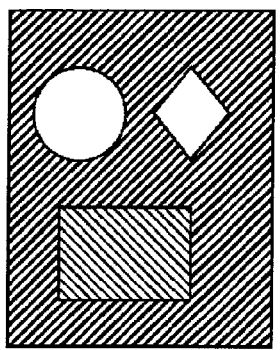
FIG. 2 is a view showing observation examples of (A) Z-contrast image and element image by characteristic X-ray spectrometer and (B) element image by electron energy loss spectrometer in the embodiment 1.
Figure 2:
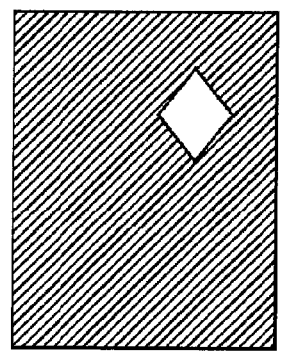
Figure 2:
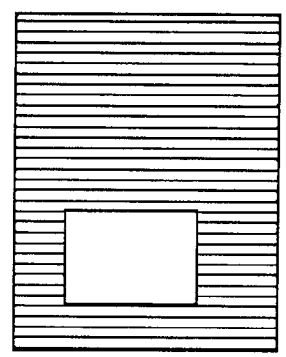

As shown in FIG. 2, elastic scattering electrons from the sample 5 are detected by the Z-contrast detector 9 as a Z-contrast image 101 corresponding to an electron beam irradiation position. Together with the Z-contrast image signal, an element image (A) 201 by the characteristic X-ray spectrometer and an element image (B) 301 by the electron energy loss spectrometer are observed.

Figure 3:
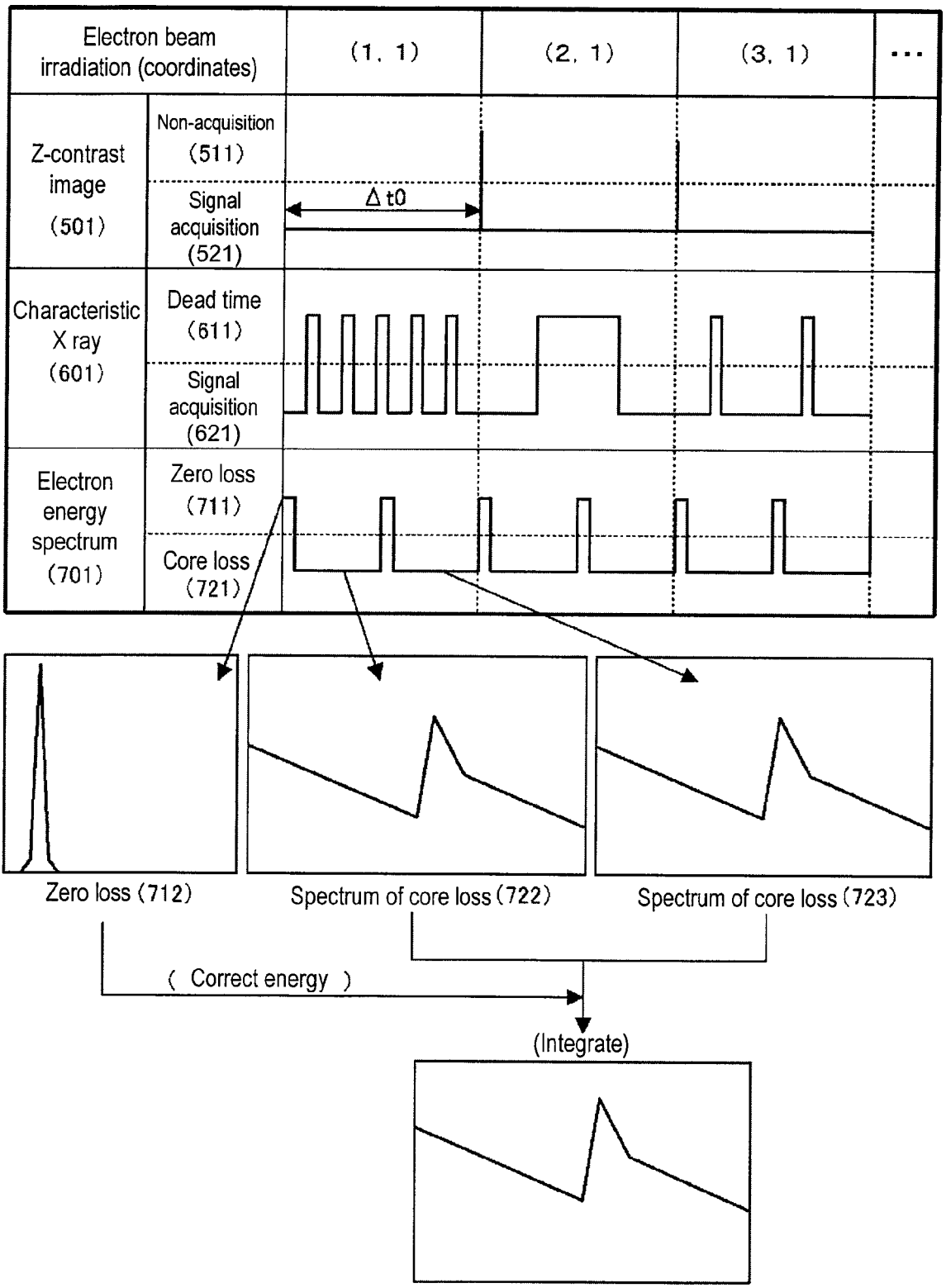
FIG. 3 is a view showing measurement time chart of electron beam irradiation time, Z-contrast image acquisition time, measurement time of a characteristic X-ray spectrum, and measurement time of an electron energy loss spectrum in the embodiment 1.

In FIG. 3, progress of time in measuring, together with the Z-contrast image signal, a characteristic-X-ray signal with the characteristic X-ray spectrometer and an electron beam energy loss signal with the electron energy loss spectrometer is shown as a time chart of electron beam irradiation in each pixel, a Z-contrast image signal detection (501), a characteristic X-ray signal detection (601), and an electron beam energy loss signal detection (701). Electron beam irradiation time ($\Delta t0$) is identical in each pixel. During electron beam irradiation, a Z-contrast signal is constantly detected (signal acquisition (521) in FIG. 3). A Z-contrast image 201 shown in FIG. 2 can be obtained by imaging an intensity signal of the Z-contrast signal.

Dead time ($\delta t\_dead$) of an output signal from the characteristic X-ray spectrometer differs depending on the amount of emitted X-rays. A time portion of the characteristic X ray (601) in FIG. 3 shown as High level is equivalent to the dead time (611). During the dead time, the characteristic X ray is not detected. Accordingly, an effectual measurement time ($\Delta t\_EDX = \Delta t0 - \delta t\_dead$) is equal to a time portion of the signal acquisition (621) shown as Low level in the characteristic X ray (601) of FIG. 3. In the Z-contrast image shown in FIG. 2, the difference in material (element) is schematically shown with a round shape, a diamond shape, and a rectangular shape. Since the dead time is dependent on materials, effectual measurement time is different in each material. A characteristic X-ray signal and a dead time are detected in each pixel and are recorded in the memory section 27 of the central control section. In the calculation section 23, the strength of a characteristic X-ray spectrum is actually corrected with the measurement time. The correcting method is standardized by, for example, dividing the strength of a characteristic X-ray spectrum by an effectual measurement time ($\Delta t\_EDX$).

The time chart of the electron energy loss spectrometer is shown in a portion of the electron energy spectrum (701) in FIG. 3. Electron beam irradiation time ($\Delta t0$) consists of a period of time for measuring an electron energy loss spectrum (core-1) including core loss of an analysis target element (core loss (721) in FIG. 3, $\Delta t\_EELS$-1) and a period of time for measuring an electron energy loss spectrum (zero) including zero loss (zero loss (711) in FIG. 3, $\delta t\_zero$). Although measurement of an electron energy loss spectrum (zero) including zero loss is conducted twice in FIG. 3 (701), the number of times of the measurement is not limited thereto and any number of times is possible as long as it is one time or more. However, the number of times of the measurement should be the same in each pixel. When the number of times to read out an electron energy loss spectrum (core-1) including core loss is the same in each pixel, read out noise of the spectrum can be made identical in each pixel. The electron energy loss spectrum (core-1) including core loss and the electron energy loss spectrum (zero) including zero loss are recorded in the memory section 27. In the calculation section 23, the amount of shift of a zero loss peak position, i.e., the amount of energy shift, is extracted from the electron energy loss spectrum (zero) including zero loss (zero loss (712) in FIG. 3). Based on the amount of energy shift, a plurality of electron energy loss spectra (core-1) including core loss (core loss spectra (722) and (723) in FIG. 3) obtained in one pixel are integrated. By this calculation, an electron energy loss spectrum with a high S/N ratio and high energy resolution is obtained.

(5) Observation of Element Image with Use of Simultaneous Measurement of Spectra with Characteristic X-Ray Spectrometer and Electron Energy Loss Spectrometer As described in section (4), a Z-contrast image, a characteristic X-ray spectrum, and an electron energy loss spectrum can be measured simultaneously at the same position. The peak intensity of an element that is an analysis target is extracted based on a characteristic X-ray spectrum, and the extracted peak intensity is used as a luminance signal of an image. As a result, an element distribution image by the characteristic X ray is obtained. When the peak intensity of the element that is an analysis target is extracted based on an electron energy loss spectrum and the extracted peak intensity is used as a luminance signal of an image, an element distribution image by the electron energy loss spectrum is obtained. The method of extracting the peak intensity of an element that is an analysis target from an electron energy loss spectrum is described in the forgoing Non Patent Literature 2.

Embodiment 2

(1) Main Differences from Embodiment 1

Figure 4:
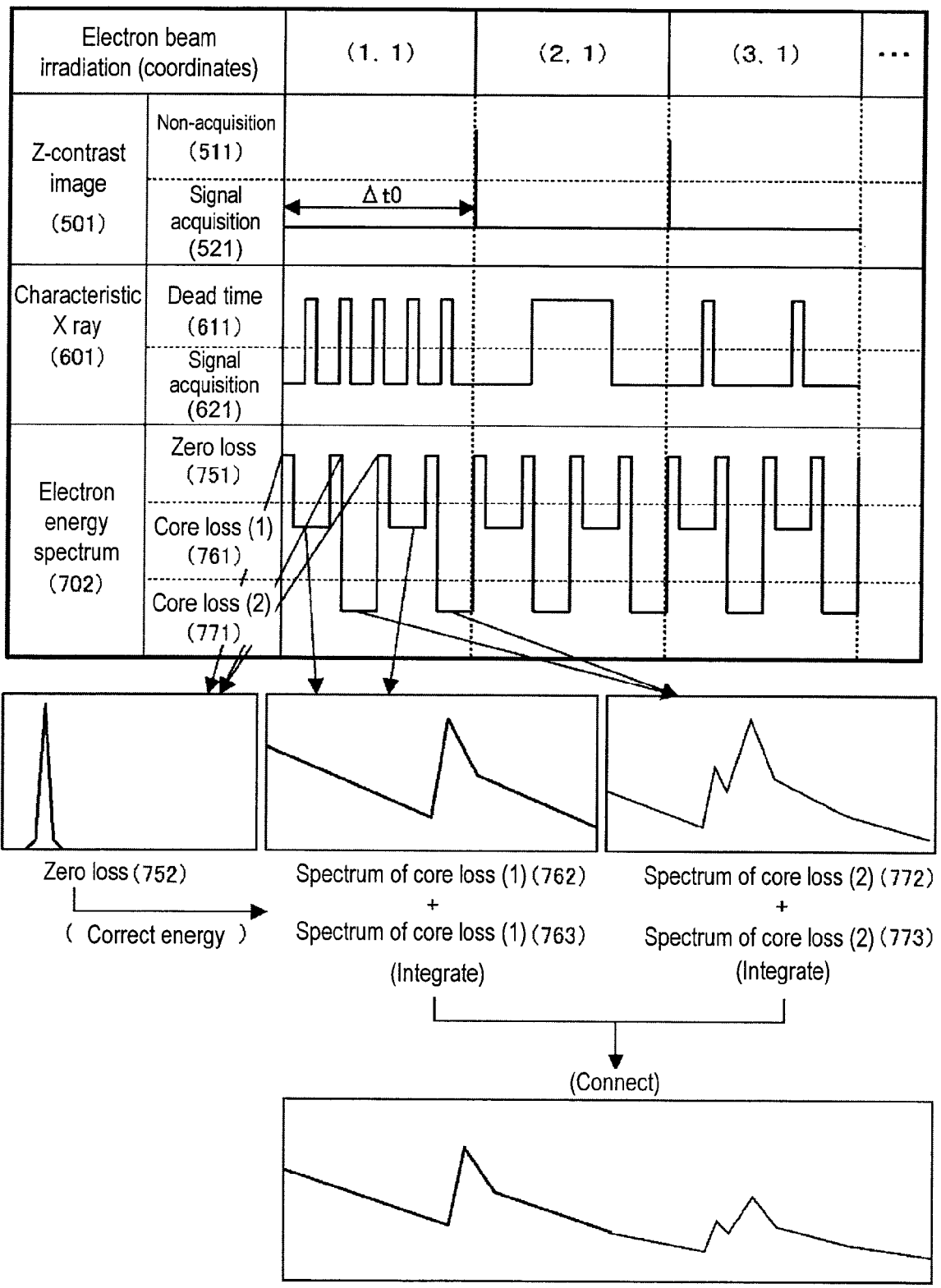
FIG. 4 is a view showing electron beam irradiation time, Z-contrast image acquisition time, measurement time of a characteristic X-ray spectrum, measurement time of two kinds of electron energy loss spectra, and an example of connecting these two kinds of electron energy loss spectra in an embodiment 2.

In the embodiment 1, measurement of an electron energy loss spectrum during electron beam irradiation in one pixel is implemented by dividing the electron energy loss spectrum into an electron energy loss spectrum (core-1) including core loss and an electron energy loss spectrum (zero) including zero loss (see FIG. 3). In the present embodiment, an electron energy loss spectrum (core-2) including core loss of another analytical element is obtained (see FIG. 4). Measurement time of the electron energy loss spectrum (core-2) including core loss of another analytical element (core loss (2) (771) in FIG. 4, $\Delta\_EELS$-2) does not need to be identical to the measurement time of the electron energy loss spectrum (core-1) including core loss of the first analytical element (core loss (1) (761) in FIG. 4, $\Delta t\_EELS$-1). The measurement time should be optimized for every target element. One example is shown in FIG. 4. Measurement of electron energy loss spectra of two kinds of elements (core loss (1) (761) and core loss (2) (771) in FIG. 4) and measurement of an electron energy loss spectrum including zero loss (zero loss (751) in FIG. 4) are performed.

Each spectrum is stored in the memory section 27. Energy correction of the spectra in the same energy range (spectra (762) and (763) of core loss (1), and spectra (772) and (773) of core loss (2) in FIG. 4) is performed based on a zero loss peak (752). Respective spectra are then integrated. The electron energy loss spectra for two kinds of elements have different energy ranges for use in measurement as shown in FIG. 4. These spectra are connected so that an electron energy loss spectrum of a broad energy range can be obtained under the spectrum measurement conditions of high resolution.

(2) Element Image Observation

As described in "(5) Observation of element image with use of simultaneous measurement of spectra with characteristic X-ray spectrometer and electron energy loss spectrometer" in embodiment 1, element distribution images can each be obtained based on the characteristic X-ray spectrum and the electron energy loss spectrum obtained in the present embodiment.

Embodiment 3

In the embodiment 1 or the embodiment 2, an electron beam irradiating a sample scans the sample surface in two dimensions so that a Z-contrast image and an element distribution image can be obtained. However, in the present embodiment, an electron beam linearly scans the sample in one dimension. When an electron beam is operated to linearly scan in one dimension, the time chart for detecting respective spectra in the characteristic X-ray spectrometer and in the electron energy loss spectrometer has only to be similar to those shown in FIG. 3 and FIG. 4. It suffices to set the coordinate of the electron beam irradiation (401) in a one-dimensional way.

REFERENCE SIGNS LIST

1 Electron beam emission source
2 Electron beam

3 Electron beam scanning coil
4 Objective lens
5 Sample
6 Characteristic X-ray spectrometer
7 Projection lens or projection lens system
9 Z-contrast detector
10 Object point
11 Electron beam
12 Multipole lens
14 Quadruple lens
15 Energy dispersion section
16 Electron beam detector
17 Energy dispersion surface
18 Drift tube
21 Control device
22 Electron energy loss spectrometer
23 Calculation section
24 Database section
25 Display device
27 Memory section
28 Electron energy loss spectrometer control section
29 Central controller
30 STEM control section
31 Input device
40 Characteristic X-ray spectrometer control section

The invention claimed is:

1. An electron microscope, comprising:
an electron beam irradiation device for irradiating a sample with an electron beam emitted from an electron beam source;
an electron energy loss spectrometer for analyzing energy of an electron beam made of inelastic scattering electrons transmitted through the sample; and
a control device for controlling the electron beam irradiation device and the electron energy loss spectrometer and obtaining an image relating to the sample, wherein the control device is configured to:
control the electron beam irradiation device so that one irradiation position on the sample is irradiated with the electron beam for a predetermined irradiation time;
divide the predetermined irradiation time into a plurality of time intervals;
obtain electron energy loss spectra for a plurality of different energy ranges within the predetermined irradiation time, wherein one electron energy loss spectrum is obtained for each of the plurality of time intervals, and the energy range for an electron energy loss spectrum for a first one of the time intervals is different from an energy range for an electron energy loss spectrum for another one of the time intervals that is time adjacent to the first one of the time intervals;
for each energy range, integrate the electron energy loss spectra obtained during the predetermined irradiation time for the respective energy range; and
connect each of the integrated electron energy loss spectra using an energy range as a transverse axis to generate a connected electron energy loss spectrum.

2. The electron microscope according to claim 1, further comprising a characteristic X-ray spectrometer for detecting a characteristic X ray emitted from the sample by irradiation of the electron beam and outputting a characteristic X-ray spectrum, wherein the control device is configured to obtain a characteristic X-ray spectrum detected by the characteristic X-ray spectrometer in the predetermined irradiation time.

3. The electron microscope according to claim 1, wherein the electron energy loss spectra obtained in the predetermined time include an electron energy loss spectrum including a core loss peak of an element that is an analysis target, and the control device is configured to obtain the electron energy loss spectrum having a same energy range a plurality of times in the predetermined irradiation time.

4. The electron microscope according to claim 1, wherein one of the electron energy loss spectra obtained in the predetermined time is an electron energy loss spectrum including a zero loss, the electron loss spectrometer includes a spectrum detector that detects an amount of energy shift between an energy reference position predefined as a zero loss reference position and a pixel position at a zero loss peak, and the control device is configured to:
correct energy of the electron energy loss spectra based on the amount of energy shift to generate corrected electron energy loss spectra;
for each energy range, integrate the corrected electron energy loss spectra obtained for the respective energy range; and
connect the corrected and integrated electron energy loss spectra to generate the connected electron energy loss spectrum.

5. The electron microscope according to claim 1, wherein the electron energy loss spectra obtained in the predetermined irradiation time include an electron energy loss spectrum including a core loss peak of an element that is an analysis target, and the control device is configured to integrate the electron energy loss spectra having a same energy range whose energy is corrected a plurality of times.

6. The electron microscope according to claim 1, wherein the electron energy loss spectra obtained in the predetermined irradiation time include a zero loss spectrum, a first core loss spectrum, and a second core loss spectrum.

* * * * *